(12) United States Patent
Winter et al.

(10) Patent No.: US 8,778,844 B2
(45) Date of Patent: *Jul. 15, 2014

(54) STRUCTURED PEPTIDE PROCESSING

(75) Inventors: Gregory Paul Winter, Cambridge (GB); Christian Heinis, Bern (CH); Elise Bernard, Cambridge (GB); David Loakes, Cambridge (GB); Marina Vaysburd, Cambridge (GB)

(73) Assignee: Bicycle Therapeutics Limited, Cambridge (GB)

( * ) Notice: Subject to any disclaimer, the term of this patent is extended or adjusted under 35 U.S.C. 154(b) by 207 days.

This patent is subject to a terminal disclaimer.

(21) Appl. No.: 13/147,257

(22) PCT Filed: Feb. 4, 2010

(86) PCT No.: PCT/EP2010/000690
§ 371 (c)(1),
(2), (4) Date: Feb. 22, 2012

(87) PCT Pub. No.: WO2010/089116
PCT Pub. Date: Aug. 12, 2010

(65) Prior Publication Data
US 2012/0142541 A1    Jun. 7, 2012

(30) Foreign Application Priority Data

Feb. 4, 2009  (WO) ................ PCT/GB2009/000301
Aug. 6, 2009  (GB) .................................. 0913775.3

(51) Int. Cl.
  *C40B 30/04*    (2006.01)
(52) U.S. Cl.
  USPC ........................................................... 506/9

(58) Field of Classification Search
None
See application file for complete search history.

(56) References Cited

FOREIGN PATENT DOCUMENTS

WO    WO 2009/098450    8/2009

OTHER PUBLICATIONS

Heinis et al. (May 31, 2009) Nature Chemical Biology vol. 5 pp. 502 to 507.*
Heinis et al. (May 31, 2009) Nature Chemical Biology vol. 5 pp. 502 to 507 Supplementary information.*
Timmerman et al. (Apr. 5, 2005) ChemBioChem vol. 6 pp. 821 to 824.*
PCT International Search Report for PCT/EP2010/000690, dated Jul. 2, 2010.
Heins, et al., "Phage-encoded combinatorial chemical libraries based on bicyclic peptides", Nature Chemical Biology, 5(7):502-07 (2009).

(Continued)

*Primary Examiner* — Christian Boesen
(74) *Attorney, Agent, or Firm* — Convergent Law Group LLP (57) ABSTRACT

The invention relates to a method for modifying one or more peptide ligands, comprising polypeptides covalently linked to a molecular scaffold at two or more amino acid residues, comprising the steps of providing one or more peptide ligands, wherein the polypeptide comprises two or more reactive groups which form a covalent linkage to the molecular scaffold, and at least one loop which comprises a sequence of two or more amino acids subtended between two of said reactive groups; exposing the peptide ligands to one or more proteases; and sorting the ligands according to the extent of proteolytic cleavage.

10 Claims, 2 Drawing Sheets

(56) References Cited

OTHER PUBLICATIONS

Cabras, et al., "HPLC-MS characterization of cyclo-statherin Q-37, a specific cyclization product of human salivary statherin generated by transglutaminase 2", J. of Separation Science, 29(17): 2600-08 (2006).

Communication pursuant to Article 94(3) EPC in EU application No. 10704 902.5 for Bicycle Therapeutics Ltd., dated Sep. 17, 2013, pp. 1-4.

Chinese Office Action for Chinese counterpart of U.S. Appl. No. 13/147,257 (app'n. No. 201080015779.4) dated Jul. 18, 2013; inventor Gregory Paul Winter; pp. 1-6.

* cited by examiner

STRUCTURED PEPTIDE PROCESSING

The invention relates to the processing of peptides whose structure is constrained by binding to a compound which provides a structural backbone, imparting a conformation to the peptide. In particular, the invention relate to the proteolytic treatment of such peptides, either to select protease resistant peptides or to select generated cleavage products.

INTRODUCTION

The generation of molecules with high affinity and specificity for biological targets is a central problem in chemistry, biology and pharmaceutical sciences. In particular, binding ligands are important for the creation of drugs that can intervene with biological processes. The creation of ligands that bind to a chosen target ligand usually involves a process of generating a plurality of putative binding molecules and testing said molecules for their binding properties.

Polypeptides tethered to a synthetic molecular structure are known in the art (Kemp, D. S., and McNamara, P. E., J. Org. Chem., 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 7 of this document shows a schematic representation of the synthesis of various loop peptide constructs. However, the peptides produced have single specificities. Where multiple peptide loops are provided, the loops cooperate to bind to a single target.

In our copending international patent application WO2009098450 we disclose the use of biological selection technology, such as phage display, to select peptides tethered to synthetic molecular structures.

The use of proteolytic treatment to modify polypeptides, including polypeptide repertoires, is known in the art. For example, GB2428293 (Domantis Limited) describes a method for reducing the valency of peptides displayed on phage by treating the phage with protease, such that the majority of the phage display no peptides, and a proportion are monovalent.

Strategies to select stably folded proteins from repertoires of phage displayed proteins based on their resistance to proteolytic degradation have been used to improve the stability of natural proteins. Proteolytic degradation is usually restricted to unfolded proteins or highly flexible regions of folded proteins. Folded proteins are mostly resistant to proteases, because the proteolytic cleavage requires the polypeptide chain to adapt to the specific stereochemistry of the protease active site, and therefore to be flexible, accessible and capable of local unfolding.

Moreover, proteases have been used in the art for generation of desired cleavage products, for example in the production of Fc, Fab and Fv antibody fragments.

We have found that protease digestion techniques can be adapted for modifying structured polypeptides tethered to synthetic molecular scaffolds, whether displayed on phage or not. These techniques enable the production not only of protease resistant structured peptides, but also of protease cleavage products in which a plurality of polypeptides remain tethered to a scaffold.

SUMMARY OF THE INVENTION

In a first embodiment, there is provided method for preparing one or more peptide ligands, comprising polypeptides covalently linked to a molecular scaffold at two or more amino acid residues, comprising the steps of:
(a) displaying one or more peptide ligand in a genetic display system, wherein the polypeptide comprises two or more reactive groups which form a covalent linkage to the molecular scaffold, and at least one loop which comprises a sequence of two or more amino acids subtended between two of said reactive groups;
(b) exposing the peptide ligands to one or more proteases; and
(c) screening the peptide ligands for binding against a target, and selecting the ligands which bind to the target.

In a related embodiment, the invention provides a method for preparing one or more peptide ligands, comprising polypeptides covalently linked to a molecular scaffold at two or more amino acid residues, comprising the steps of:
(a) displaying one or more peptide ligand in a genetic display system, wherein the polypeptide comprises two or more reactive groups which form a covalent linkage to the molecular scaffold, and at least one loop which comprises a sequence of two or more amino acids subtended between two of said reactive groups;
(b) screening the peptide ligands for binding against a target, and selecting the ligands which bind to the target;
(c) exposing the peptide ligands which bind to the target to one or more proteases; and
(d) further screening the peptide ligands for binding against a target.

Applicable systems include phage display, bacterial display, yeast display, ribosome or polysome display, mRNA display and in vitro expression in artificial microcapsules. An mRNA display system is described in Litovchick et al., PNAS Oct. 7, 2008 vol. 105 no. 40; 15293-15298. The preferred technique is phage display using a filamentous bacteriophage.

The peptide ligand is selected for the ability to bind to one or more targets. The ligands may be monospecific, in that they bind to a single target, or multispecific, that is capable of binding to two or more different targets. Multispecific ligands can be in an open conformation, in which they can bind two or more different targets simultaneously, or in a closed conformation, in which they can only bind one target at any one time.

Peptide ligands comprise at least one polypeptide loop, formed by the amino acid sequence subtended between the at least two reactive groups attached to the molecular scaffold. Preferably, the peptide ligands comprise two or more loops, and may comprise three, four or more loops. For example, the polypeptide may comprise 3 or more reactive groups, between which are subtended two or more loops. A polypeptide comprising three reactive groups will support two loops in a linear form, or three loops if circularised.

A particular application of the method of the invention is to create repertoires of peptide ligands. Such repertoires can be created, for example, by displaying repertoires of polypeptides on phage and subsequently conjugating them to molecular scaffolds, as described in WO2009098450.

Proteolysis can be used to modify the peptides in situ on the ligands, or to select those conjugates which are resistant to proteolytic attack. In a first configuration, therefore, the invention relates to the selection of protease resistant peptide ligands. Such ligands are useful in environments where proteases are present, such as at mucosal surfaces. In this configuration, the invention is particularly useful with repertoires of conjugates, which can screened and sorted according to their protease resistance.

The repertoire may be naïve at the time of proteolytic treatment, and the proteolysis-resistant members selected from the repertoire can be screened for binding to one or more targets after proteolytic treatment.

In such an embodiment, the method preferably further comprises: optionally, treating the repertoire with reducing agent; subjecting the repertoire to selection for protease resistance; screening said repertoire for binding against a target, and selecting members of the first repertoire which bind to the target.

In another embodiment, the repertoire can be screened for binding to one or more targets before proteolytic treatment.

In such an embodiment, the method further comprises the steps of screening said repertoire for binding against a target, and selecting members of the first repertoire which bind to the target before treatment with a protease; optionally, treating the selected repertoire with a reducing agent; subjecting the repertoire to selection for protease resistance; and subsequently further screening said repertoire for binding to the target.

The invention moreover relates to a repertoire of polypeptides, each polypeptide comprising two or more reactive groups covalently linked to a molecular scaffold, and at least one loop which comprises a sequence of two or more amino acids subtended between two of said reactive groups, which repertoire is protease resistant.

As noted above, such a repertoire may be naïve, or may have been selected for binding to one or more targets. Selection for target binding may take place before selection for protease resistance, after selection for protease resistance, or both.

According to a second configuration of the invention, peptide ligands may be treated by proteolysis in order to generate cleaved polypeptides immobilised on to the scaffolds. In such an embodiment, the method further comprising selecting the peptide ligands which are susceptible to protease cleavage.

For example, the procedure can generate ligands comprising two or more separate polypeptides, each of which is attached to a molecular scaffold at least one position. This can leave the polypeptides relatively free of conformational constraint.

In one embodiment, the method may be performed with a repertoire of peptide ligands.

The invention moreover provides a repertoire of peptide ligands, each conjugate comprising two or more polypeptides each comprising one or more reactive groups covalently linked to a molecular scaffold.

Preferably, the peptide ligands are capable of specifically binding one or more targets.

Suitably, the peptide ligands are multispecific.

The conjugates are advantageously displayed on a genetic display system, such as phage display.

In a further aspect, the invention provides a method for modulating the binding of a peptide ligand to one or more targets comprising exposing the peptide ligand to a protease.

Proteolytic cleavage can be used to select ligands which are protease resistant. such ligands are useful in medical applications, where it may be necessary to operate in a protease-rich environment. For example, the peptide ligands of the invention may act as ligands for molecules of the immune system, for example as antigens. They can therefore be useful as vaccines, adjuvants and immunotherapeutic drugs. In another embodiment, however, cleavage can be specifically directed to cleave specific loops of a peptide, thereby altering the binding characteristics of the ligand.

In one embodiment, one or more loops of the ligand may bind to their designated target(s) only when uncleaved, and conformationally influenced by attachment to the scaffold. In this case, protease treatment can be used to prevent binding by a particular loop to its designated target. For example, if the peptide ligand is bispecific, one or other of the loops may be cleaved to prevent binding to the relevant target, by including a specific protease cleavage site in the desired loop and exposing the ligand to the cognate protease.

In such an embodiment, specific proteases can be selected to modulate the binding activity of one or more peptide ligands for one or more targets. Thus, a given ligand could be rendered bispecific or monospecific, by protease cleavage of one or more loops.

In another embodiment, one or more loops of the ligand may bind to their designated target(s) only when cleaved, and substantially free of conformational restriction from the scaffold to which they remain attached. In this embodiment, cleavage can be used selectively to promote binding of a loop to its designated target.

DETAILED DESCRIPTION OF THE INVENTION

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

A peptide ligand, as referred to herein, refers to a peptide covalently bound to a molecular scaffold. Typically, such peptides comprise two or more reactive groups which are capable of forming covalent bonds to the scaffold, and a sequence subtended between said reactive groups which is referred to as the loop sequence, since it forms a loop when the peptide is bound to the scaffold.

The reactive groups are groups capable of forming a covalent bond with the molecular scaffold. Typically, the reactive groups are present on amino acid side chains on the peptide. Preferred are amino-containing groups such as cysteine, lysine and selenocysteine.

Proteolysis is the cleavage of a polypeptide by a proteolytic enzyme, referred to as a protease. Suitable proteases include trypsin (cleaves at Lys, Arg), chymotrypsin (Phe, Trp, Tyr, Leu), thermolysin (small aliphatic residues), subtilisin (small aliphatic residues), Glu-C (Glu), Factor Xa (Ile/Leu-Glu-Gly Arg), Arg-C (Arg) and thrombin. In one embodiment, since the potentially random polypeptide sequence in repertoires cannot be guaranteed to generate a precise cleavage site for a particular protease, a protease capable of cleaving at a variety of sites is used.

Where the cleavage of a specific sequence is required, a more specific protease can be used. Specific proteases are described further below.

Protease resistance is used to indicate increased resistance to proteolytic cleavage. For example, such resistance can be achieved through modification of the primary sequence of the peptide, or of the polypeptide backbone. For example, alterations in the primary sequence can remove the cleavage site for the protease, as long as the alterations do not involve residues which make key contacts for target binding. With peptides displayed on phage, alterations are made most readily with one of the 20 amino residues encoded by nucleic acid. With peptides made by chemical synthesis, a range of other side chains can be used, for example changing lysine to ornithine or arginine to citrulline, or the like.

Preferably, a protease resistant peptide is 2, 3, 4, 5, 10, 20 times or more, more resistant to proteolytic cleavage that an unmodified peptide.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands are capable of binding to two or more targets and are therefore multispecific. Preferably, they bind to two targets, and are dual specific. The binding may be independent, which would mean that the binding sites for the targets on the peptide are not structurally hindered by the binding of one or other of the targets. In this case both targets can be bound independently. More generally it is expected that the binding of one target will at least partially impede the binding of the other.

Multispecific peptides can be formed by joining together individual loops of peptide ligands which bind to individual targets. The loops which are joined together may be adjacent lops, or may be separated by a third loop, or even further loops. Where the loops are placed directly adjacent in the multispecific peptide, it is preferred that one of the reactive groups defining one of the loops is omitted, to avoid effective duplication of reactive groups at one position.

A target is a molecule or part thereof to which the peptide ligands bind. Typically, the target will be analogous to an epitope, and thus may take the form of different epitopes on the same molecule, or different epitopes on different molecules. Where the targets are on the same molecule, the use of a dual specific ligand will increase the avidity of the ligand for the molecule, and may impart other properties due to cross-linking the molecule or the occupation of defined functional parts of the molecule.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Preferably, the molecular scaffold comprises at least three attachment points for the peptide, referred to as scaffold reactive groups. These groups are capable of reacting to the reactive groups on the peptide to form a covalent bond. Preferred structures for molecular scaffolds are described below.

A repertoire is a collection of variants, in this case polypeptide variants, which differ in their sequence. Typically, the location and nature of the reactive groups will not vary, but the sequences forming the loops between them can be randomised. Repertoires differ in size, but should be considered to comprise at least $10^2$ members. Repertoires of $10^{11}$ or more members can be constructed.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, each of which has a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members.

Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

Preferably, a library of nucleic acids encodes a repertoire of polypeptides. Each nucleic acid member of the library preferably has a sequence related to one or more other members of the library. By related sequence is meant an amino acid sequence having at least 50% identity, suitably at least 60% identity, suitably at least 70% identity, suitably at least 80% identity, suitably at least 90% identity, suitably at least 95% identity, suitably at least 98% identity, suitably at least 99% identity to at least one other member of the library. Identity is suitably judged across a contiguous segment of at least 3 amino acids, suitably at least 4, 5, 6, 7, 8, 9 or 10 amino acids, suitably least 12 amino acids, suitably least 14 amino acids, suitably least 16 amino acids, suitably least 17 amino acids or the full length of the reference sequence.

A functional group, attached to a peptide ligand, is a group which, for example, mediates a further binding activity or permits the binding of an effector group. Thus, functional groups include antibodies and binding fragments thereof, further peptide ligands as described herein, chemical reactive groups, and the like.

An effector group is a group attached to the peptide ligand which has a specific activity. For instance, it may be a protein which increases the half life of the peptide ligand, such as human serum albumin (HSA). Effector groups also include drugs, such as cytotoxic drugs, immunoeffectors, such as antibody Fc regions, and compounds which conform to the following parameters: not more than 5 hydrogen bond donors (nitrogen or oxygen atoms with one or more hydrogen atoms); not more than 10 hydrogen bond acceptors (nitrogen or oxygen atoms); a molecular weight under 500 daltons; and an octanol-water partition coefficient log P of less than 5.

A. Peptide Ligands

The design and production of peptide ligands is described in our published International patent application WO 2009/098450, as well as International patent applications WO 2004/077062 and WO 2006/078161. The following aspects summarise constructing peptide ligands.

(i) Molecular Scaffold

The molecular scaffold is sometimes referred to as the 'molecular core' or 'connector compound'. Suitably, the molecular scaffold possesses molecular symmetry. Suitably, the molecular scaffold possesses three scaffold reactive groups and possesses threefold symmetry. This has the advantage of producing only a single reaction product. If the molecular scaffold is not a symmetric molecule, then multiple reaction products can be produced. This can lead to complications, or require that the desired isomer be separated from the other reaction products.

Suitably the molecular scaffold may be a small molecule. Suitably the molecular scaffold is a small organic molecule.

Suitably the molecular scaffold may be, or may be based on, natural monomers such as nucleosides, sugars, or steroids. Suitably the molecular scaffold may comprise a short polymer of such entities, such as a dimer or a trimer.

Suitably the molecular scaffold may comprise or may consist of tris(bromomethyl)benzene, especially 1,3,5-Tris(bromomethyl)benzene ('TBMB'), or a derivative thereof.

Another suitable molecular scaffold is 2,4,6-Tris(bromomethyl)mesitylene. It is similar to 1,3,5-Tris(bromomethyl)benzene but contains additionally three methyl groups attached to the benzene ring. This has the advantage that the additional methyl groups may form further contacts with the polypeptide and hence add additional structural constraint.

The molecular scaffold of the present invention is selected from either a small molecule or a macromolecular structure. The said molecular scaffold is composed of organic, inorganic or organic and inorganic components.

In a preferred embodiment, the molecular scaffold is a small organic molecule as for example a linear alkane. More suitably the molecular scaffold is a branched alkane, a cyclic alkane, a polycyclic alkane, an aromate, a heterocyclic alkane or a heterocyclic aromate, which offer the advantage of being less flexible (i.e. more rigid). Most suitably the molecular scaffold comprises a benzylic group.

In another embodiment, the molecular scaffold is selected from a macromolecular structure as for example a polypeptide, a polynucleotide or a polysaccharide.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

(ii) Polypeptide

The reactive groups of the encoded polypeptides are suitably provided by side chains of natural or non-natural amino acids. The reactive groups of the encoded polypeptides are suitably selected from thiol groups, amino groups, carboxyl groups, guanidinium groups, phenolic groups or hydroxyl groups. The reactive groups of the encoded polypeptides may suitably be selected from azide, keto-carbonyl, alkyne, vinyl, or aryl halide groups. The reactive groups of the encoded polypeptides for linking to a molecular scaffold may suitably be the amino or carboxy termini of the polypeptide.

In some embodiments each of the reactive groups of the polypeptide for linking to a molecular scaffold are of the same type. For example, each reactive group may be a cysteine residue.

Suitable amino acids of the members of the genetically encoded combinatorial chemical libraries can be replaced by any natural or non-natural amino acid. Excluded from these exchangeable amino acids are the ones harbouring functional groups for cross-linking the polypeptides to a molecular core. A group of adjacent amino acids that can be varied is defined as a polypeptide segment. The size of a single polypeptide segment suitably ranges from 1 to 20 amino acids. The polypeptide segments have either random sequences, constant sequences or sequences with random and constant amino acids. The amino acids with reactive groups are either located in defined or random positions within the encoded polypeptide of the invention.

In one embodiment, the polypeptide segments that are bounded by two amino acids harbouring reactive groups for bonding with a molecular scaffold/molecular core are short amino acid sequences of 10 or fewer amino acids. Reaction of said encoded polypeptide sequences with a molecular core generates library members with high conformational constraint. Conformational constrained ligands are generally more specific and have higher binding affinities.

(iii) Reactive Groups of the Polypeptide

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group.

Suitably at least one reactive group is a cysteine group. Groups such as lysine or the N-terminal amines are typically not reactive enough to bond with the molecular scaffold on their own within a convenient time frame. However, once the molecular scaffold has been attracted or bonded to at least one cysteine, then ordinary reaction kinetics mean that the lysine or amine bonds can rapidly and stably form thereafter. For this reason, suitably at least one of the reactive groups is a cysteine group.

If reactive groups on the polypeptide other than cysteine/lysine/amine groups are desired, then a different molecular scaffold may be chosen in order to pair with the particular functional reactive groups of choice on the target polypeptide.

Suitably cysteine, lysine or amine groups are used as the functional or reactive groups on the polypeptide of interest.

Suitably at least three covalent bonds are formed between the molecular scaffold and the polypeptide of interest.

In some embodiments, four bonds or even more may be formed between the molecular scaffold and the polypeptide of interest. However, if more than four bonds are used, then typically the product mixtures formed become increasingly complex and may hinder the subsequent uses or applications.

For this reason, three bonds or four bonds between the molecular scaffold and the polypeptide of interest are preferred.

Suitable reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The encoded polypeptides of the invention suitably contain at least three reactive groups. Said polypeptides can also contain four or more reactive groups. The more reactive groups are used, the more diversity segments can be tethered to the molecular scaffold/molecular core. However, the linkage of excessive numbers of reactive groups to a molecular scaffold/molecular core is not recommended since this can lead to an unmanageable number of product isomers. Suitably three, four or five covalent bonds to a molecular scaffold are used; most suitably three or four covalent bonds; most suitably three covalent bonds.

B: Attachment of Scaffolds to Phage Peptides

Detailed conditions for the attachment of scaffolds to phage peptides without destroying phage infectivity are described in our international patent application WO 2009/098450. The attachment of scaffold molecules involves the following principles.

In particular, the reduction of the cysteines in the target polypeptide is required for the most efficient reaction. Subsequently, the reducing agent used to chemically reduce those cysteines is usually removed in order to perform the desired attachment. Thiol groups of a phage encoded polypeptide may be reduced with reducing agent prior to molecular scaffold attachment. In such embodiments, in particular in phage display embodiments, or in particular when the reducing agent is TCEP, the excess of reducing agent is suitably removed by filtration e.g. filtration of the phage. However in some embodiments, the reducing agent can be present during the attachment at levels that do not react with the molecular scaffold sufficiently to compromise the reaction of the molecular scaffold with the cysteines of the peptide.

Re-oxidation of the thiol groups can be prevented by including TCEP in the reaction of the peptide with the molecular scaffold.

Re-oxidation of the thiol groups is suitably prevented by degassing of the reaction buffer.

Re-oxidation of the thiol groups is also suitably prevented by complex formation of metal ions by chelation, for example chelation with ethylenediaminetetraacetic acid (EDTA).

Most suitably re-oxidation of the thiol groups is prevented or inhibited by including TCEP in the reaction of the molecular scaffold, by chelation and by use of degassed buffers.

In one embodiment of the present invention, attachment of the polypeptide to the molecular scaffold is accomplished by reacting the reactive groups of the polypeptide such as thiol groups of a phage encoded polypeptide with the molecular scaffold for one hour.

Suitably they are reacted at 30° C.

Suitably they are reacted with molecular scaffold (such as tris(bromomethyl)benzene) at a concentration of 10 μM to 40 μM.

Suitably reaction is in aqueous buffer.

Suitably reaction is at pH 8.

Suitably reaction buffer contains acetonitrile. Suitably reaction buffer contains 20% acetonitrile.

These reaction conditions are optimized to quantitatively react thiol groups of a polypeptide with the reactive groups of tris(bromomethyl)benzene. Under the same reaction conditions, about 20% of the phage particles remain infective to bring the genetic code into bacterial cells for propagation and decoding.

In one embodiment the molecular scaffold, such as TBMB, may be attached to the target polypeptide, such as a phage encoded polypeptide, by reaction (incubation) of thiol groups of the polypeptide for one hour at 30° C. with 10 μM TBMB (i.e. tris(bromomethyl)benzene) in the presence of 10 μM TCEP in aqueous buffer pH 8 containing 20% acetonitrile. In another embodiment, the reaction can be carried out using 40 μM TBMB in the presence of 30 μM TCEP in the same buffer.

C: Proteolytic Cleavage

Protease Cleavage

In some embodiments, the polypeptide elements of the invention are proteolytically cleaved once they are tethered to a molecular scaffold/molecular core. The cleavage generates ligands having discrete peptide fragments tethered to a molecular scaffold/molecular core.

For example, one or more amide bonds of the polypeptide may be proteolytically cleaved after tethering the polypeptide to the molecular core. This has the advantage of creating short polypeptides, each joined to the molecular scaffold by at least one covalent bond, but which present different molecular structures which are retained in a complex comprising the nucleic acid encoding the parent polypeptide. The polypeptide cleavage is suitably catalysed by any suitable means known in the art such as controlled hydrolysis or more suitably enzymatic cleavage by a suitable protease. The protease may be any suitable protease but is preferably a protease with a specific polypeptide recognition sequence or motif. This advantageously leads to production of more defined and/or more predictable polypeptide cleavage products. Indeed, in this embodiment, protease recognition sequences may be systematically added or removed from the target polypeptide, for example by manipulation of the nucleic acid(s) encoding it. This advantageously provides a greater degree of control and permits greater diversity to be produced in the molecules displayed according to the present invention. Most suitably the polypeptide comprises at least one protease recognition site. Suitably each said cleavage site is comprised within amino acid sequence(s) in between reactive groups on the polypeptide used for covalent bonding to the molecular scaffold. Suitably each said recognition site is comprised within amino acid sequence(s) in between reactive groups on the polypeptide used for covalent bonding to the molecular scaffold.

The peptide loops are suitably cleaved with a protease that recognizes and processes polypeptides at specific amino acid positions such as trypsin (arginine or lysine in P1 position) or thermolysin (aliphatic side chains in P1 position). The enzyme is used at a concentration that allows efficient processing of the peptide loops of the displayed molecule but spares the phage particle. The optimal conditions can vary depending on the length of the polypeptide loops and on the protease used. Trypsin for example is typically used at 200 nM in TBS-Ca buffer (25 mM Tris HCl/137 mM NaCl/1 mM $CaCl_2$, pH 7.4) for 10 min at 10° C. A whole range of proteases that are suitable to modify displayed polypeptides but that spare the phage are described in Kristensen, P. and Winter, G. (Proteolytic selection for protein folding using filamentous bacteriophages; Fold Des. 1998; 3(5):321-8). The enzymatic processing of peptide on phage may be a 'partial proteolysis' since it can not be excluded that a limited number of phage coat proteins are cleaved. Thus in optimisation of the conditions, the best balance between maximised cleavage of the target and maximum sparing of the phage particles is suitably chosen.

Suitably the target polypeptide comprises at least one such proteolytic cleavage site. Suitably the target polypeptide comprises at least two such proteolytic cleavage sites.

Suitably the target polypeptide comprises at least three such proteolytic ceavage sites.

In each such proteolysis embodiment, suitably the said protease site(s) are located within the target polypeptide loops subtended by the molecular scaffold. This has the advantage that the molecular scaffold is retained on the complex, as otherwise the polypeptide-molecular scaffold complex may be separated from the nucleic acid encoding the target polypeptide, which is undesirable for the majority of applications of the invention.

The use of short loops (short being e.g. 6 amino acid residues or less) may compromise the ability of some proteases to cleave within the loops. In some cases, therefore, it may be desirable to select longer loops which are likely to be more accessible to the protease. Furthermore after cleavage of the loops by endoprotease, it may be desirable to cut back the loops further with other endoproteases, or indeed by exoproteases, such as carboxypeptidases or aminopeptidases.

When the target polypeptide comprises more than one such protease site, suitably each of the sites occurs between two covalent bonds made between the target polypeptide and the molecular scaffold. Multiple cleavage sites may occur between bonds if necessary.

Protease Resistance

In another embodiment, the polypeptides may be resistant to protease cleavage. In general, tightly folded polypeptide structures are more resistant to proteases, since the protease cannot physically access the polypeptide to cleave it. Therefore, manipulation of the scaffold and scaffold attachment in the peptide ligand can modulate protease sensitivity, by influencing the folding of the polypeptide loop.

As indicated in the preceding section, a protease step can be introduced to cleave accessible sites within loops attached to a chemical scaffold. If a repertoire of peptide conjugates is displayed on phage, this leads to peptides each joined to the chemical scaffold by at least one covalent bond, but retained in a complex comprising the nucleic acid encoding the parent polypeptide. The treatment of the chemically modified phage with protease before selection with antigen is expected to give rise to phage bearing peptide conjugates with cleaved loop(s), and also to phage bearing peptide conjugates with uncleaved loop(s) due to lack of a cleavage site, or otherwise being resistant to cleavage. It is possible to distinguish these species if one binds to antigen and the other does not, by comparing the binding of the selected phage clones to target antigen before and after protease treatment. Thus the species with cleaved loops will be expected to bind after protease treatment, but not before; whereas the protease-resistant species will be expected to bind both before and after treatment. Note that if a conjugate binds with both cleaved and uncleaved loops (as with PK15 after kallikrein cleavage; see Heinis et al, 2009), it may be incorrectly identified as protease resistant. This shows the importance of using a direct method for checking cleavage, for example by synthesizing the peptide conjugates chemically, and checking for evidence of cleavage, for example by mass spectrometry.

If cleaved loop conjugates are preferred to protease resistant conjugates, it will be advantageous to treat the chemically modified phage repertoire with protease before the first round of selection, and to continue to use the same protease, or one with a common cut-site, in subsequent rounds. However protease resistant conjugates may alternatively be desired. Such peptides may be useful for oral administration to survive the gut proteases, or those otherwise subject to proteolytic attack in the blood, tissues or cells. Protease resistant therapeutics can moreover be administered at lower dosages. In this case, a first round of selection without protease, followed by a subsequent round of selection with protease, should favour the selection of the resistant species.

The use of protease has further utility during the selection process. For example, some unformed loops (linear segments of sequence) may be present in the libraries because (a) errors in the synthesis of the nucleotides have failed to encode a required cysteine residue, or (b) a required cysteine residue has made a disulphide bond to free cysteine in solution (perhaps due to inadequate reduction or re-oxidation), or has reacted in an irreversible manner (for example is oxidized to cysteic acid, or one of the required cysteines has reacted with a different molecule of the scaffold to the others). As linear segments of sequence are more susceptible to protease attack than loops, then, subject to a cleavage site being present, it may be possible to avoid such binders using protease.

A protease step (in the presence of reducing agent) is also advantageous to eliminate loops that have formed via disulphides between the required cysteines rather than through the chemical scaffold. This may be expected if there is inadequate reduction (or subsequent reoxidation) of the cysteines on the phages. For this reason we used degassed buffers during the chemical cross-linking step; we also kept low levels of the reducing agent (TCEP) during the reaction with TBMB to maintain the reducing environment. Nevertheless, after the first round of selection, we found many sequences that included four cysteine residues (the three required cysteine residues, and a further cysteine residue in the loop), for example PEP21 (CFNSEWSCLQSCSNC) (SEQ ID No. 1. Such extra cysteines are expected to be present in the peptide repertoires, as the synthetic nucleotide library includes random codons (NNK diversity: where N represents a 25% mix each of adenine, thymine, guanine, and cytosine nucleotides, and K represents a 50% mix each of thymine and guanine nucleotides). Under some conditions, for example if there is inadequate reduction, or incomplete reaction of the required cysteines with the chemical scaffold (perhaps due to competing reactions for the scaffold by amino groups or water), an extra cysteine may be expected, under oxidising conditions, to form disulphide loops with one of the three required cysteines. Alternatively an extra cysteine may react with the scaffold, leaving two of the required cysteines to form disulphide-closed loops.

Whatever the exact mechanism behind their generation, such disulphide-closed loops may compete with the scaffold-closed loops, and predominate. It should be possible to reduce the frequency of the extra cysteines by using synthetic nucleotide libraries built from triplets, rather than monomers, so avoiding cysteine codons in the loops; and/or to undertake the selections in the presence of reducing agent, so as to open the disulphide-closed loops. More conveniently we have found that the treatment of the chemically modified phage repertoires with protease in the presence of reducing agent (such as dithiothreitol or TCEP), so as to open and then cleave the loops, helps to minimise the contribution of such species.

In one embodiment, therefore, the peptide ligands of the invention are substantially protease resistant. Exposing the peptide ligands to cleavage after selection against the target will favour the identification of binding peptide ligands which are resistant to protease cleavage. However it cannot be excluded that certain peptide ligands will retain the ability to bind to the target after cleavage. The invention therefore provides a method for selecting a peptide ligand having increased protease resistance, comprising the steps of:

(a) providing a first repertoire of polypeptides;
(b) conjugating said polypeptides to a molecular scaffold which binds to the polypeptides at two or more amino acid residues, to form a repertoire of polypeptide conjugates;
(c) screening said repertoire for binding against a target, and selecting members of the first repertoire which bind to the target;
(d) optionally, treating the selected repertoire with reducing agent
(e) treating the repertoire with a protease; and
(f) further screening said repertoire for binding to the target.

In another embodiment, the peptide ligands of the invention are substantially cleaved by protease. The protease step is included before the screening of repertoire, which will favour the identification of peptide ligands which bind to the target in cleaved form. The invention therefore provides a method for selecting a peptide ligand that is cleaved by protease, comprising the steps of:

(a) providing a first repertoire of polypeptides;
(b) conjugating said polypeptides to a molecular scaffold which binds to the polypeptides at two or more amino acid residues, to form a repertoire of polypeptide conjugates;
(c) optionally treating the repertoire with reducing agent
(d) treating the repertoire with a protease; and
(e) screening said repertoire for binding against a target, and selecting members of the first repertoire which, after treatment with protease, bind to the target.

A screen for protease resistance can simply take the form of limited digestion with a protease to identify those members of the repertoire in which the binding is sensitive to proteases, or requires the action of proteases. Most desirable will be to use a protease that is active under the conditions in which the bicyclic peptide will be used, for example in the presence of serum.

Conditions for Protease Cleavage

In one aspect, cleavage of peptides displayed on phage can take place at a defined protease cleavage site. A cleavage site is a position in the sequence of the peptide where a protease is able to cleave the linear peptide. For example, such a site may be naturally present in a peptide displayed on phage, whether due to random mutagenesis or choice of peptides which comprise cleavage sites.

Alternatively, the cleavage site may be engineered into the peptide, for example by directed mutagenesis of the nucleic acid encoding the peptide.

The cleavage site can be an enzymatic cleavage site such as that cleaved by a protease such as thrombin, Factor Xa, an enteropeptidase such as serine protease, enterokinase (including those described in WO 01/98366), or for example by trypsin, or it can be a chemical cleavage site cleavable by chemicals such as CNBr which cleaves at a methionine residue.

Preferably, enzymatic cleavage agents are used. it is important to balance the cleavage of the peptide in the ligand with cleavage of the phage, which will destroy phage infectivity.

There exist a number of highly specific proteases. While the invention does not reside in the choice of any particular protease, the protease is preferably sufficiently specific under the conditions used so that under said cleavage conditions, it has the ability to cleave the cleavage site in the peptide ligand but not any polypeptide essential to the viability of the phage. Selection of particular cleavage conditions, e.g., low temperature, make it feasible to use a protease that would otherwise be unsuitable.

The blood-clotting and complement system contains a number of very specific proteases. Usually, the enzymes at the early stages of cascade are more specific than are the later ones. For example, Factor X, (FX) is more specific than thrombin. Bovine FX cleaves after the sequence Ile-Glu-Gly-Arg (SEQ ID No. 2) while human FX cleaves after Ile-Asp-Gly-Arg (SEQ ID No. 3). Either protease-linker pair may be used, as desired.

If thrombin is used, thrombin-sensitive sites are found in fibrinogen, Factor XIII, and prothrombin. The species from which the FX is derived will influence the precise specificity of the protease, which is adapted to cleave the precise sequences found in its natural targets in vivo.

Human Factor XI cleaves human Factor IX at two places: QTSKLTR/AEAVF (SEQ ID No. 4) and SFNDFTR/VVGGE (SEQ ID No. 5). Such a protease therefore provides a very specific cleavage system, which will cleave peptides only at a very limited number of sites.

Human kallikrein cuts human FXII at R353: LFSSMTR/WGFLV (SEQ ID No. 6).

This sequence has significant similarity to the hFXI sites above.

Human FXII cuts human FXI at R369: KIPPR/IVGGT (SEQ ID No. 7).

Other proteases that have been used to cleave fusion proteins include enterokinase, trypsin, collagenase, chymosin, urokinase, renin, and certain signal peptides. See Rutter, U.S. Pat. No. 4,769,326 which is herein incorporated by reference.

In a preferred embodiment of the invention, the protease is any one in the group selected from the following: PreScission™ which recognises and cleaves the cleavage site LEV-LFQGP (SEQ ID No. 8); factor Xa which cleaves the site IEGRGI (SEQ ID No. 9); and thrombin which cleaves the site LVPRGS (SEQ ID No. 10) and the site LVPKGS SEQ ID No. 11).

Those skilled in the art will appreciate that the cleavage conditions must be carefully controlled such that phage is not inactivated by cleavage of essential phage polypeptides. As noted above, a whole range of proteases that are suitable to modify displayed polypeptides but that spare the phage are described in Kristensen, P. and Winter, G. (Proteolytic selection for protein folding using filamentous bacteriophages; Fold Des. 1998; 3(5):321-8).

D: Targets

Peptide ligands according to the present invention may be designed to bind to any given target. One skilled in the art will appreciate that the choice of target molecule is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA78, Eotaxin, Eotaxin-2, Exodus-2, FGF-acidic, FGF-basic, fibroblast growth factor-10, FLT3 ligand, Fractalkine (CX3C), GDNF, G-CSF, GM-CSF, GF-I, insulin, IFNy, IGF-I, IGF-II, IL-Ia, IL-1 (3, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-17a, IL-17c, IL-17d, IL-17e, IL-17f, IL-18 (IGIF), IL-21, IL-22, IL-23, IL-31, IL-32, IL-33, IL-34, Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a. a.), MDC (69 a. a.), MCP-1 (MCAF), MCP-2, MCP-3, MCP-4, MDC (67 a. a.), MDC (69 a. a.), MIG, MIP-Ia, MIP-1p, MIP-3a, MIP3, MIP-4, myeloid progenitor inhibitor factor-1 (MPIF-1), NAP-2, Neurturin, Nerve growth factor, P-NGF, NT-3, NT-4, Oncostatin M, PDGF-AA, PDGF-AB, PDGF-BB, PF-4, RANTES, SDFIa, SDFIp, SCF, SCGF, stem cell factor (SCF), TARC, TGF-α, TGF-β, TGF-2, TGF-3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4; Cytokine receptors include receptors for the foregoing cytokines. Chemokine targets include CC chemokine ligands CCL21/6Ckine, CCL12/MCP-5, CCL6/C10, CCL22/MDC, CCL14/HCC-1/HCC-3, CCL3L1/MIP-1 alpha Isoform LD78 beta, CCL23/Ck beta 8-1, CCL3/MIP-1 alpha, CCL28, CCL4L1/LAG-1, CCL27/CTACK, CCL4/MIP-1 beta, CCL24/Eotaxin-2/MPIF-2, CCL15/MIP-1 delta, CCL26-like/Eotaxin-3-like, CCL9/10/MIP-1 gamma, CCL26/Eotaxin-3, CCL19/MIP-3 beta, CCL11/Eotaxin, CCL20/MIP-3 alpha, CCL14a/HCC-1, CCL23/MPIF-1, CCL14b/HCC-3, CCL18/PARC, CCL16/HCC-4, CCL5/RANTES, CCL1/I-309/TCA-3, TAFA1/FAM19A1, MCK-2, TAFA5/FAM19A5, CCL2/JE/MCP-1, TAFA3/FAM19A3, CCL8/MCP-2, TAFA4/FAM19A4, CCL7/MCP-3/MARC, CCL17/TARC, CCL13/MCP-4 and CCL25/TECK; chemokine receptors include CCR1, CCR7, CCR2, CCR8, CCR3, CCR9, CCR4, CCR10, CCR5, CCRL2/LCCR/CRAM-A/B and CCR6; CXC chemokine ligands include CXCL13/BLC/BCA-1, CXCL10/IP-10/CRG-2, CXCL14/BRAK, LIX, CXCL16, CXCL15/Lungkine, CXCL5/ENA-78, CXCL9/MIG, CXCL6/GCP-2, CXCL7/NAP-2, CXCL1/2/3/GRO, CXCL4/PF4, CXCL1/GRO alpha/KC/CINC-1, CXCL12/SDF-1 alpha, CXCL2/GRO beta/MIP-2/CINC-3, CXCL12/SDF-1 beta, CXCL3/GRO gamma/CINC-2/DCIP-1, CXCL12/SDF-1, CXCL11/1-TAC, CXCL7/Thymus Chemokine-1 and CXCL8/IL-8; CXC chemokine receptors include CXCR3, CXCR7/RDC-1, CXCR4, CXCR1/IL-8 RA, CXCR5, CXCR2/IL-8 RB and CXCR6; TNF Superfamily ligands include 4-1BB Ligand/TNFSF9, LIGHT/TNFSF14, APRIL/TNFSF13, Lymphotoxin, BAFF/BLyS/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA (pan), TNF-beta/TNFSF1B, EDA-A1/Ectodysplasin A1, TRAIL/TNFSF10, EDA-A2, TRANCE/TNFSF11, Fas Ligand/TNFSF6, TWEAK/TNFSF12 and GITR Ligand/TNFSF18; TNF Superfamily receptors include 4-1BB/TTNFRSF9/CD137, NGF R/TNFRSF16, BAFF RfTNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACl/TNFRSF13B, DcR3/TNFRSF6B, TNFRH3/TNFRSF26, DcTRAIL R1/TNFRSF23, TNF RI/TNFRSF1A, DcTRAIL R2/TNFRSF22, TNF RII/TNFRSF1B, DR3/TNFRSF25, TRAIL R1/TNFRSF10A, DR6/TNFRSF21, TRAIL R2/TNFRSF10B, EDAR, TRAIL R3/TNFRSF10C, Fas/TNFRSF6/CD95, TRAIL R4/TNFRSF10D, GITR/TNFRSF18, TROY/TNFRSF19, HVEM/TNFRSF14, TWEAK R/TNFRSF12, Lymphotoxin beta R/TNFRSF3 and XEDAR; Toll-Like Receptors including TLR-1, TLR-2, TLR-3, TLR-4, TLR-5, TLR-6, TLR-7, TLR-8 and TLR-9; enzymes, including Cathepsin A, Cathepsin B, Cathepsin C, Cathepsin D, Cathepsin E, Cathepsin F, MMP 1, MMP2, MMP 3, MMP 7, MMP 8, MMP 9, MMP 10, MMP 11, MMP 12, MMP 13, MMP 14, MMP 15, MMP 16, MMP 17, MMP 19, MMP 20, MMP 21, MMP 23A, MMP 23B, MMP 26, MMP 27, MMP 28, urokinase, kallikreins, including KLK1, KLK2, KLK3, KLK4, KLK5, KLK6, KLK7, KLK8, KLK9, KLK10, KLK11, KLK12, KLK13, KLK14 and KLK15; components of the complement system; Intracellular signalling molecules and transcription factors; p53; and MDM2.

It will be appreciated that this list is by no means exhaustive.

Targets may also be large plasma proteins, such as serum albumins, as set forth below.

Where the polypeptide conjugate binds to two epitopes (on the same or different targets), the target molecules may be selected from this list. The targets may compete for binding to the polypeptide conjugate, such that they cannot both bind simultaneously. Alternatively, they may both bind simultaneously, such that the polypeptide conjugate bridges the targets.

Targets may be bound by the ligand when the peptide loop(s) are cleaved, or uncleaved. Thus, in one embodiment, one or more targets is only bound when at least one loop of the peptide ligand is uncleaved and the peptide assumes a structure constricted by binding to the scaffold. Cleavage of the ligand in the appropriate loop results in abolition of binding. If the ligand is bispecific, binding to one or other, or both, of the targets can be modulated by cleavage of one or more loops as appropriate.

Conversely, the ligand may bind to target(s) when one or more loops is cleaved, and the peptide acts as an aptamers-like molecule which binds to its target when substantially free of conformational restriction imposed by the scaffold. In such an embodiment, cleavage of the loops induces binding.

Accordingly, by cleaving one or more loops with an appropriate protease, the binding of the ligands to one or more targets can be modulated.

In another embodiment, protease resistant ligands can be selected for use in binding targets such as proteases, or for use in protease-rich environments, such as in plasma or mucosal surfaces.

Such ligands are useful in medical applications, such as vaccines, therapeutic agents and diagnostics.

EXAMPLES

The invention is further described with reference to the following examples.

Example 1

Protease Resistant Bicyclic Peptides Against MDM2

MDM2 is an enzyme (an E3 ubiquitin ligase) that recognises the trans-activation domain of p53, the tumour suppressor, leading to ubiquitinylation and degradation of p53 by the proteosome. A nutlin inhibitor of the p53-MDM2 interaction can lead to in vivo activation of the p53 pathway, and it has been suggested that such agents may have potential as anti-cancer agents. Here we describe the selection of two bicyclic peptides (PEP10 and PEP48) against MDM2, a target "antigen". The affinity of each synthetic peptide was sub-micromolar, and in the range 250-750 nM. At least one of the peptides was shown by competition ELISA to bind to the same site as a linear peptide previously shown to block the p53-MDM2 interaction.

Protocols generally followed those described earlier in Heinis et al., 2009, Nature Chemical Biology 5, 502-507, unless otherwise indicated. In the work of Heinis et al., both targets, kallikrein and cathepsin G, were proteases, and the kallikrein inhibitor is fairly resistant to proteolysis by kallikrein, although it includes a kallikrein cleavage site. MDM2 is not a protease, and therefore it was not clear whether the selected peptides would also be resistant to protease. For this, and other reasons (for detail see below), we included one or more protease (chymotrypsin) steps after reaction of the phage peptide repertoires with the TBMB (including under reducing conditions) and before selection of the repertoire against MDM2. The two selected phage peptides PEP10 and PEP 48 appear resistant to proteolysis, as shown by phage ELISA.

Phage Production and Purification

The phage peptide library with diversity of at least $4 \times 10^9$ clones was prepared and TBMB conjugated as described earlier with a few modifications.

1. The cx6 library of phage as described earlier (which had been prepared from TG1 cells) was used to infect the non-suppressor strain HB2151 (Carter, Bedouelle & Winter. 1985. Nucleic Acids Res. 13:4431-43), and the infected cells plated. The bacteria were scraped from the plates in about 8 ml 2×TY medium, 30 ug/ml chloramphenicol, 10% glycerol (v/v).
2. About 0.8 ml of the stock was added to 800 ml 2×TY medium with 30 ug/ml chloramphenicol to obtain an OD of about 0.1 at 600 nm. The culture was incubated at 30° C., and shaken in a 2 liter flask at 200 rpm for 16 hrs.
3. The cell culture was centrifuged at 4,000 rpm (Heraeus Megafuge 2R) for 30 min at 4° C. The supernatant was transferred to 200 ml cold 20% PEG, 2.5 M NaCL. The mixture was left on ice for 1 hr.
4. The precipitated supernatant/phage mixture was spun down for 30 min at 4° C. and the supernatant was discarded.
5. The phage was resuspended in 35 ml PBS, 5 mM EDTA followed by spinning for 15 min at 4000 rpm (Heraeus Megafuge 2R) to remove cellular debris. The supernatant was transferred into a new 50 ml Falcon tube.

Modification of Phage with TBMB 1. 5 ml of 8 mM TCEP (in $H_2O$) was added to the phage to obtain a final concentration 1 mM TCEP. The tube was inverted several time to mix and incubated for 1 hr at 42° C. water bath.
2. The TCEP was removed by a second PEG precipitation. 10 ml of 20% PEG, 2.5 M NaCL (degassed solution) was added, mixed, and incubated on ice for 45 min and spun for 30 min at 4000 rpm, 4° C.
3. The supernatant was carefully removed and pellet resuspended in 12 ml PBS, 5 mM EDTA, 10 uM TCEP (degassed buffer)
4. 3 ml of 50 uM TBMB in acetonitrile was added to the 12 ml of reduced phage to obtain a final TBMB concentration of 10 uM. The tube was inverted several times and left at 30° C. for 1 hr in a water bath. The phage were cooled on ice and precipitated with ⅕ volume of 20% PEG, 2.5 M NaCL for 30 min. The phage were collected by spinning at 4000 rpm (Hereaus Megafuge 2R) for 20 min. Supernatant was removed and the phage resuspended in 4 ml of PBS. Phage was transferred into the 2 ml Eppendorf tubes and spun at 13000 rpm (Eppendorf benchtop centrifuge) for 10 min. Supernatant was transferred into a new Eppendorf tube and phage infectivity was measured.

Phage Selection: General Protocol

First Round of Selection

1. Purified and chemically conjugated phage as above was selected against biotinylated MDM2 (bio-MDM2) peptide (res 2-125) immobilized on the surface of the streptavidin-coated Dynabeads (Dynal Biotech). 80 µl of beads were first washed and blocked with 2% (w/v) Marvell milk powder in PBS (PBSM) for 40 min followed by incubation with 100 nM bio-MDM2 for 20 min in a total volume of 1 ml.
2. Chemically modified phage ($10^{10}$-$10^{11}$ TU) was incubated with PBSM for 40 min.
3. Blocked Ag-coated beads from step 1 were washed from the excess of the Ag with 0.1% Tween in PBS (PBST) and incubated with the blocked phage for 30 min in a total volume of 1 ml.
4. Unbound phage were washed with 10× with PBST followed by 2× with PBS. After each third washing step the phage coated beads were transferred into a new Eppendorf tube.
5. Phage were eluted by incubating with 500 µl of 50 mM glycine pH 2.2 for 10 min on a rotating wheel. Eluted phage were neutralized with 250 µl of 1M Tris, pH7.5.
6. 375 µl of phage was incubated with 10 ml of HB2151 cells for 90 min at 37° C. without shaking.
7. The infected cells were then shaken for 30 min at 37° C. and then plated on a chloramphenicol plate (20×20 cm).
8. The colonies were scraped off the plate in 2×TY, chloramphenicol, 10% glycerol as described above, and stored as a glycerol stock at −80° C. A fraction of the cells was used to prepare phage for the second round of selection.

Second Round of Selection

The second round of selection was similar to the first one except for a few modifications.

1. Neutravidin-coated magnetic beads were used instead of streptavidin ones.
2. The amount of antigen used in the selection was 20 nM.
3. Chemically modified phage ($10^{10}$-$5 \times 10^{10}$ TU) was first treated with 50 ug/ml of chymotrypsin for 2 min followed by blocking with PBSM for 40 min.
4. Unbound phage was washed with 15× with PBST followed by 2× with PBS, otherwise as above.

Phage Selection: Variant Protocol

Clone 48 was selected using the general protocol as above, whereas clone 10 was developed as a result of a modified protocol being introduced. The modifications are the following:

1. In the first round chemically modified phage were pretreated with 50 ug/ml of chymotrypsin for 2 min followed by blocking with PBSM for 40 min.
2. In the second round chemically modified phage were first reduced with 5 mM DTT for 20 min followed by incubation with 50 ug/ml of chymotrypsin for 2 min and blocking with PBSM for 40 min.

Peptide Synthesis

The encoded peptides from phage clone 48 and phage clone 10 were synthesized with free N- and C-termini.
PEP10: H-Ser-Cys-Glu-Leu-Trp-Asn-Pro-Lys-Cys-Arg-Leu-Ser-Pro-Phe-Glu-Cys-Lys-Gly-OH (SEQ ID No. 12);
PEP48: H-Ser-Cys-Val-Arg-Phe-Gly-Trp-Thr-Cys-Asp-Asn-Ser-Trp-His-Gly-Cys-Lys-Gly-OH (SEQ ID No. 13).

The syntheses was performed by Fmoc-peptide synthesis on a CEM Liberty microwave peptide synthesizer on 0.1 mmol Fmoc-Gly-PEG PS resin using a 5-fold excess of Fmoc-amino-acids activated with PyBop in DMF and DIPEA in NMP (1 equivalent and 2 equivalents respectively. Side-chain protecting groups were as follows: Arg(Pbf); Asn(Trt); Asp(OtBu); Cys(Trt); Glu(OtBu); Lys(Boc); Ser(tBu); Thr (tBu); Trp(Boc). Fmoc-deprotection was carried out using 20% v/v Piperidine/DMF containing 0.1M HOBt. The H-peptidyl-resins were washed with DMF, then propan-2-ol and dried in vacuo. Cleavage of side-chain protecting groups and from the support was effected using 94:2.5:2.5:1 v/v/v/v TFA/EDT/H$_2$O/iPr$_3$SiH for 2 hours. The peptide/TFA mixture was filtered to remove the support and the peptide/TFA mixture was diluted with water and washed with Et$_2$0 (5-times) and the aqueous layer lyophilized.

Reverse-phase hplc were performed on a Phenomenex Jupiter 5μ C18 300 Å 250×4.6 mm column. Buffer A: 0.1% TFA/H20; Buffer B: CH3CN containing 10% Buffer A. The column was eluted isocratically with 10% Buffer B for 2 minutes, then with a linear gradient of 10-90% over 25 minutes. Detection was at 215/230 nm; flow rate of 1.5 ml/min.

The peptides were lyophilized and checked by mass spectrometry. PEP10 MALDI-TOF mass (M+H): 2099.9 Da (Theory: 2098.4 Da.) PEP48 MALDI-TOF Mass (M+H): 2043.8 Da (Theory: 2042.8 Da.). The peptides were then conjugated with TBMB.

Synthesis of TBMB-Peptide Conjugates

Initial reactions were performed to mimic the conditions used during phage selection. Typically, 5 mg of the purified peptide was dissolved in 1 ml water and 0.8 ml 50 mM NH$_3$HCO$_3$ added, followed by 40 μl of TCEP. TBMB (3 equivalents based on weight of peptide) dissolved in MeCN was added to the reaction. The reaction was left for 1.5 hrs then monitored by HPLC. On completion the reaction was purified by HPLC. Typically 0.5 to 1.5 mg of final product was obtained. This method gives rise to many by-products, the major product being the desired mass+250 amu. This corresponds to addition of TCEP to the desired product, and that the yield of this product increases with reaction time. In addition other higher mass products corresponding to addition of a second TBMB were observed by MALDI-TOF mass spec, but were not isolated.

Based on the formation of TCEP adducts a preferred method was developed. Following cleavage of the peptide from the resin, it was either purified directly by HPLC or pre-treated with TCEP for 15 mins prior to HPLC purification. The product from the HPLC reaction, in the HPLC elution buffer (typically 6 ml) is neutralised with 50 mM NH$_3$HCO$_3$ (4 ml) and TBMB added in MeCN as above. The addition of 10% THF results in a clear solution and therefore accelerates the reaction. Reactions are monitored by mass spec, but typically are complete in 1-2 hrs. There are minimal by-products from this reaction (though the presence of product+16 is observed by mass spec). The reaction requires concentration to remove organic solvents prior to HPLC purification otherwise the product tends to elute with the solvent front. Yields of product from this method are typically 0.5 to 1.5 mg from 3 mg peptide, but this has not been optimised.

Binding Assays

Phage ELISA Assay 0.6 μg/mL of biotinylated MDM2 peptide (res 2-125) was immobilized on a streptavidin-coated plate (Roche). Plate was blocked with PBSM (but 4% in milk powder) and linear or TBMB-conjugated phage (10$^7$ TU/well in PBSM in the presence or absence of 5 mM DTT) was incubated on the plate for 50 min at room temperature. Similarly, phage was first reduced in 5 mM DTT for 20 min, treated with chymotrypsin (50 ug/ml in PBS) for 2 min, mixed with PBSM (final concentration) and incubated on the plate for 50 min at room temperature. Phage was detected using an anti-M13-HRP monoclonal antibody (1:5000, Amersham).

Figure 1:
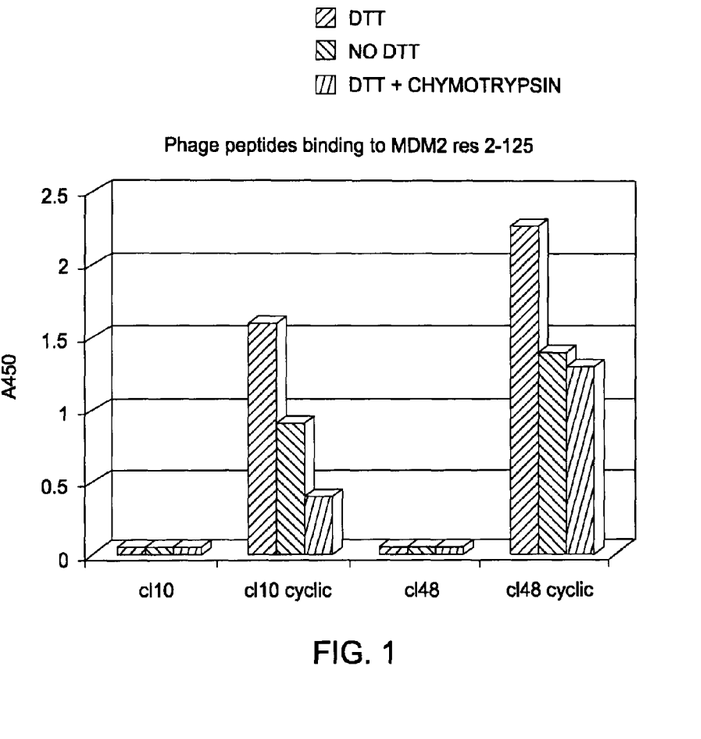
FIG. 1 shows binding of phage clones 10 and 48 (Example 1) to MDM2 as cyclic conjugates or unconjugated peptides, without pre-treatment with DTT, and with pre-treatment with DTT, and with pre-treatment with DTT followed by chymotrypsin.

The results (FIG. 1) showed qualitatively that both phage clones 10 and clone 48 bind to MDM2 as the cyclic conjugate but not as the unconjugated peptide (whether or not pre-treated with DTT). Furthermore the binding of the conjugated peptide resists proteolysis. Note that 5 mM DTT can reduce the disulphide bonds of chymotrypsin leading to its inactivation as a protease. To ensure that the chymotrypsin was active under the conditions of the assay, we incubated control phage bearing a linear peptide that binds MDM2 after pre-treatment as above with 5 mM DTT. Under the conditions of our experiment, the binding activity of the control phage was lost on proteolysis. In other experiments we have used up to 0.2 mM-5 mM TCEP in the presence of chymotrypsin (0.1 mg/ml-1 mg/ml) for 2 minutes at room temperature in PBS. These conditions also allowed us to distinguish between the linear and cyclic peptides on phage.

Fluorescence Anisotropy Measurements

Titration experiments were run on a Horiba Jobin Yvon fluorimeter equipped with the Hamilton Microlab titrator controlled by laboratory software. The $\lambda_{ex}$ and $\lambda_{em}$ used were 295 nm and 350 nm, respectively. The slit widths for excitation and emission were 5 nm and 15 nm and the integration time 10 s was used for each measurement. The intrinsic fluorescence of tryptophan in peptides 10, 48 was used to measure their binding affinity for MDM2 (res 2-125). The experiments were performed at 23° C. in PBS, 5 mM DTT. Usually 250 μl of MDM2 (150 uM) was titrated into 1.2 ml of peptide (1 uM). Titration data were analyzed with a standard 1:1 binding model by using the quadratic solution to the equilibrium Kd=[A][B]/[AB]. Kd is the dissociation rate, and [A] and [B] refer to the concentration of a titrant (MDM2) and fluorescent peptides 10 and 48, respectively. The fitting equation contained an extra term to account for linear drift.

Figure 2:
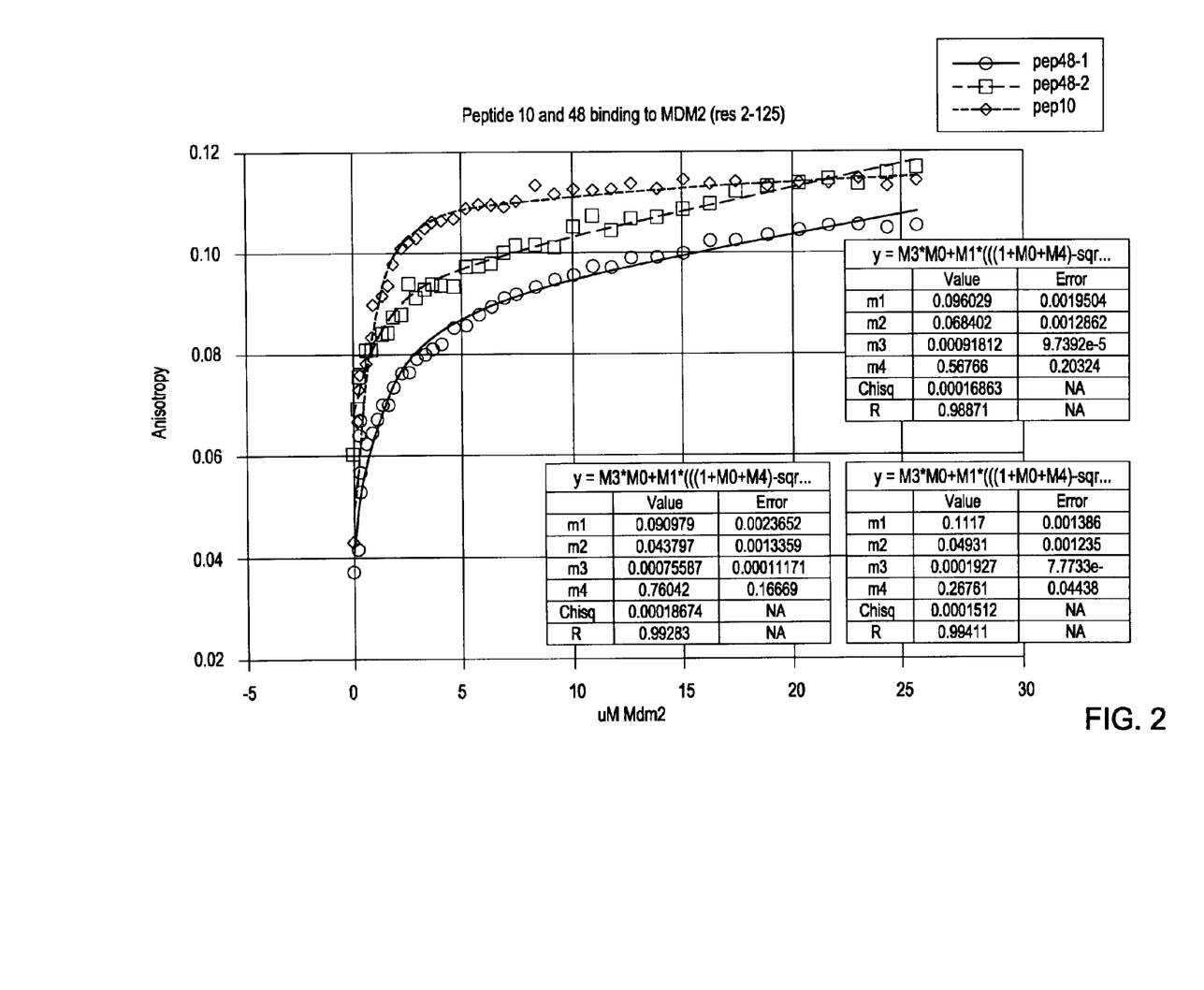
FIG. 2 shows a fluorescence anisotropy plot for peptides PEP10 and PEP48, indicating the affinity for MDM2. See Example 1.

The results (FIG. 2 and below) indicate that the affinity of each peptide is sub-micromolar, and in the range 250-750 nM. The measurements for PEP48 were repeated.

PEP10+MDM2, measured λex=295 nm, Kd=267 nM; PEP48+MDM2, measured λex=280 nm, Kd=760 nM; PEP48+MDM2, measured λex=295 nm, Kd=567 nM Competition Assays The binding of PEP48 phage to MDM2 was competed by a peptide pMI (TSFAEYWNLLSP) that binds to MDM2 at the p53 site with a Kd=3.3 nM (Pazgier et. al., 2009 PNAS, 106, 4665-4670). 0.6 μg/ml of biotinylated MDM2 peptide (res 2-125) was immobilized on a streptavidin-coated plate (Roche). Plate was blocked with PBSM. TBMB-conjugated phage (10$^7$ TU/well in 1% PBSM) was premixed with a range of concentrations of pDI (from 6.94 nM to 1 uM) and incubated on the plate for 75 min at room temperature. Phage was detected using an anti-M13-HRP monoclonal antibody (1:5000, Amersham). The binding of PEP48 phage to MDM2 was inhibited by addition of the pMI peptide, with an estimated IC50=125 nM.

Example 2

Protease Resistance of Bicyclic Peptides

The bicyclic peptides PK15 and CG4 of Heinis et al., 2009, were selected against the proteases kallikrein and cathepsin G respectively, and it would not be surprising if the bicyclic peptides are resistant to digestion by these proteases, particularly the constrained nature of the scaffold should help protect against proteolytic attack.

We compared PK15 linear (cysteines treated with iodoacetamide) with PK15 conjugated to the TBMB scaffold, with kallikrein and with other proteases, see Table below (the scale ranges from +++ (substantially intact) to − (completely cleaved). As expected the PK15 conjugate with TBMB was more resistant than the linear to attack by kallikrein. The factor was about 100 fold, as shown by comparing different concentrations of enzyme.

For the other proteases, the factor ranged between 10 and 100 fold, depending on the protease. We also compared the resistance of the bicyclic CG4L1-PK15L1 (WO 2009/098450) to proteolysis. In this case the factor ranged between 1 and more than 100 fold, depending on the protease. Thus the conjugate has an increased resistance to proteases other than to the protease (kallikrein) that it was exposed to during the selection process.

The variation of resistance according to the protease suggests that it is desirable to include a proteolysis step in the selection or the screening process, as already described in Example 1. Most desirable will be to use a protease that is active under the conditions in which the bicyclic peptide will be used, for example in the presence of serum. For interest we checked the resistance of PK15 to serum. This showed that the linear PK15 is digested by the proteases in serum at 37° C. within about 2 hours. However the PK15 conjugate resists proteolysis for at least 48 hours; later times have yet to be tested.

TABLE

Peptide conjugate digestion with various proteases.

|  | PK15 linear | PK15-TBMB | CG4L1-PK15L1 linear | CG4L1-PK15L1 TBMB |
|---|---|---|---|---|
| Cathepsin G |  |  |  |  |
| 1 | − | ++ | − | ++ |
| 0.1 | − | +++ | − | +++ |
| 0.01 | +/ | +++ | − | +++ |
| Chymotrypsin |  |  |  |  |
| 10 | − | ++ | − | − |
| 1 | − | +++ | − | + |
| 0.1 | + | +++ | − | ++ |
| 0.01 | +++ | +++ | ++ | +++ |
| Kalikrein |  |  |  |  |
| 1 | − | +++ | − | ++ |
| 0.1 | + | +++ | − | +++ |
| 0.01 | +++ | +++ | − | +++ |
| Pronase |  |  |  |  |
| 10 | − | + | + | ++ |
| 1 | +/− | ++ | ++ | +++ |
| 0.1 | ++ | +++ | ++ | +++ |
| 0.01 | +++ | +++ | +++ | +++ |
| Proteinase K |  |  |  |  |
| 10 | − | ++ | − | +/− |
| 1 | +/− | +++ | + | + |
| 0.1 | + | +++ | + | + |
| 0.01 | ++ | +++ | ++ | ++ |
| Subtilisin |  |  |  |  |
| 9 | − | − | − | − |
| 0.9 | − | + | − | +/− |
| 0.09 | ++ | ++ | − | + |
| 0.009 | +++ | +++ | − | +++ |
| Trypsin |  |  |  |  |
| 10 | − | − | − | − |
| 1 | − | + | − | + |
| 0.1 | +/− | ++ | − | ++ |
| 0.01 | + | +++ | +/− | +++ |

Numbers correspond to number of µg enzyme per reaction

Methods

For methods, see Example 3 following. The proteolysis was undertaken at 37° C. Cathepsin G and kalikrein reactions were carried out in 10 mM Tris pH 7.4, 150 mM NaCl, 10 mM MgCl$_2$, 1 mM CaCl$_2$, 0.1% BSA, 0.01% Triton X100, 5% DMSO. Chymotrypsin reactions were carried out in 100 mM Tris pH 7.4, 10 mM CaCl$_2$. Pronase and proteinase K reactions were carried out in 100 mM Tris pH 7.4, 0.5% SDS. Subtilisin reactions were carried out in 50 mM KH$_2$PO$_4$ pH 7.5. Trypsin reactions were carried out in 67 mM sodium phosphate pH 7.6. Reaction conditions with serum involve dissolving the peptide in 1×PBS (total volume 24 µl) and 6 µl of human serum added to the reaction.

Example 3

Trypsin and Chymotrypsin Cleavage Sites of PK15

To identify the trypsin and chymotrypsin cleavage sites of PK15, we used both the iodoacetamide-derivatized peptide and the TBMB conjugate, as described above in Example 2. The proteolysis conditions were also as described in Example 2. By mass spectrometric analysis, from analysis of the molecular masses of the cleaved species, we were able to show that in the iodoacetamide derivatized peptide (AC*SDRFRNC*PADEALC*G) (SEQ ID No. 14) R7 and R9 were both cleaved by trypsin, and F8 cleaved by chymotrypsin. The same cleavage sites were seen in the TBMB conjugated peptide, except that the cleavages were at a much slower rate as noted in Example 2. Furthermore with trypsin, the initial cleavage step was at R7, followed in longer incubations by cleavage at R9.

Methods

Peptides and conjugates were purified on a Proteo C12 (4µ, Phenomenex) column using a Varian 940 HPLC. Buffers used were 0.1% TFA (A) and 90% MeCN, 0.1% TFA (B). Generally samples were eluted in a 10-65% buffer B gradient over 23 minutes.

For the TBMB conjugation we used our general conditions, which are as follows. 5-6 mg of the crude peptide after synthesis (see Example 1 for typical synthesis conditions) was dissolved in 600 µl water (adding 20 µl of 10% ammonia solution if insoluble) followed by 60 µl TCEP and allowed to stand for 20 mins. In two injections the reduced peptide was purified by HPLC (conditions above) collecting the peptide in ca 3-4 ml elution buffer. The solution was neutralised with an equal volume of 100 mM ammonium phosphate buffer and 1 ml acetonitrile added. 10 equivalents of TBMB was dissolved in 1 ml acetonitrile and added to the reduced peptide. The pH was monitored and further 100 mM ammonium phosphate buffer added if the pH was acidic. Generally reactions were complete within 20-30 minutes. The reaction was then purified by HPLC, loading first up to 4.5 ml of the reaction onto the column equilibriated in 0.1% TFA, washing for 8 mins with 0.1% TFA then eluting from the column as below. Pure fractions were lyophilised and dissolved in water (10% DMSO if insoluble). Products and reactions are monitored throughout by MALDI-TOF mass spectrometry, desalting reaction mixtures using a ZipTip. Yields of conjugate were typically 1-2 mg.

For the iodoacetamide conjugates we used our general conditions which are as follows. After synthesis, the crude peptides (5-6 mg) were dissolved in water (600 µl) and treated with TCEP (60 µl of 0.5M) for 20 minutes prior to HPLC. The purified fraction from HPLC (ca 3 ml) was neutralized with and equal volume of 100 mM ammonium bicarbonate and treated with 10 equivalents of iodoacetamide in 1 ml MeCN. Under these conditions reactions are usually complete within 30 minutes. The reaction mixture was purified by HPLC directly, loading up to 4.5 ml of the mixture onto the column equilibriated in 0.1% TFA, washed with 0.1% TFA for 8 minutes and then eluted as described earlier.

Peptides (linear and conjugates) were dissolved in water at a concentration of 1 mg/ml, giving an effective concentration of ~0.5 mM stock solutions and the concentration determined using amino acid analysis. 2 μl of peptide conjugates (20 μM final concentration) (~30 μM in reactions depending on actual molecular weight) were dissolved in reaction buffer (see below) in a total reaction volume of 30 μl, followed by the protease (typically in the range 1, 0.1 and 0.01 μg per reaction), and samples were incubated at 37° C. for 1 hr. 10 μl aliquots were quenched into 10 μl of 1% TFA. Samples were analysed by MALDI-TOF mass spectrometry to identify the fragment peaks and thus determine the site of cleavage. Where there was ambiguity as to the cleavage site samples were analysed by either by MALDI-TOF-TOF (Bruker Ultraflex 3) or by Linear Ion Trap (Thermoscientific Orbitrap XL) to determine accurate masses.

Example 4

Backbone Changes to Resist Proteolysis

The PK15 bicycle conjugate is more resistant to digestion by chymotrypsin and trypsin than the linear form as described in Example 2. However after extended incubation it is cleaved at the arginine residues by trypsin and after phenylalanine by chymotrypsin, as described in Example 3. By making changes in amino acid side chains, it may be possible to provide further resistance to proteolysis. It may also possible to do so by making changes in the peptide backbone as described here and exemplified by introduction near the sites of cleavage, of a D-amino acid, or N-methylation, or a reduced peptide bond. Thus to provide resistance at the protease cleavage sites of PK15 the following variants were synthesized:

H-ACSDR f RNCPADEALCG-OH (where f represents D-Phe) (SEQ ID No. 15), and H-ACSDRF-(NMeArg)-NC-PADEALCG-OH (SEQ ID No. 16), and H-ACSDRF Y[CH$_2$NH] RNCPADEALCG-OH (where the Y[CH$_2$NH] represents the reduced peptide bond) (SEQ ID No. 17).

In the following descriptions of peptide synthesis, the abbreviations are as follows. THF: tetrahydrofurane; NMM: N-methylmorpholine; IBCF: iso-butylchloroformate; DMF: N,N-dimethylformamide; DiPEA: diisopropylethylamine; TFA: trifluoroacetic acid; EDT: ethane dithiol; PyBOP: benzotriazole-1-yl-oxy-tris-pyrrolidino-phosphonium hexafluorophosphate; PyBrOP: bromo-tris-pyrrolidino-phosphonium hexafluorophosphate The D-Phenylalanine peptide (H-ACSDR f RNC-PADEALCG-OH) (SEQ ID No. 15) was synthesized as described in Example 1, adding D-Phe in place of L-Phe.

The NMe-Arginine peptide, H-ACSDRF-(NMeArg)-NC-PADEALCG-OH (SEQ ID No. 16), was synthesized on a CEM Liberty automated peptide synthesizer as described in Example 1 up to the amino acid preceding the NMeArginine. The resin was taken up in a syringe and after deprotection of the Fmoc group, 6 equivalents of Fmoc-NMe-Arg(Mtr)-OH, 6 equivalents of PyBOP and 12 equivalents of DiPEA were dissolved in 4 mL DMF. The solution was added to the resin and stirred for 40 minutes. The step is reproduced for a double coupling. Then Fmoc-deprotection was carried out using 20% v/v Piperidine/DMF. After washings with DMF (4-times), 6 equivalents of Fmoc-Phe-OH, 6 equivalents of PyBrOP and 12 equivalents of DiPEA were dissolved in 4 mL DMF. The solution was added to the resin and stirred for 3 hours. The step is reproduced for a double coupling. Then the resin is washed with DMF and put back on a CEM Liberty peptide synthesizer to complete the sequence. Cleavage of side-chain protecting groups and from the support was effected using 82.5:5:5:5:2.5 v/v/v/v/v TFA/Phenol/Thioanisole/water/EDT overnight. The peptide/TFA mixture was filtered to remove the support and the peptide/TFA mixture was diluted with water and washed with Et20 (5-times) and the aqueous layer lyophilized.

The peptide with reduced peptide bond, H-ACSDRF Y[CH$_2$NH] RNCPADEALCG-OH (SEQ ID No. 17), first required the preparation of Fmoc-phenylalaninal. 5 mmol of Fmoc-Phe-OH were dissolved in 10 mL anhydrous THF and kept at −15° C. under nitrogen. 5 mmol of NMM and 5 mmol of IBCF were then added. After 15 min, the suspension was filtered and rinsed with 2×5 mL anhydrous THF. 5 mmol of morpholine was added dropwise to the filtrate and after one hour, the reaction was complete. The mixture was concentrated in vacuo and ethyl acetate was added. The organic layer was washed with a solution of KHSO$_4$ 5%, then a solution of KHCO$_3$ 5% and distilled water, dried over magnesium sulfate and concentrated in vacuo. The Weinreb amide obtained was purified by silica gel flash chromatography. Then 1.95 mmol of the compound was dissolved in 20 mL anhydrous THF and placed in an ice bath under nitrogen. 1.25 eq of LiAlH$_4$ was added and the reaction was checked by TLC of an aliquot separately hydrolysed with aquous KHSO$_4$. After 45 min, the reaction was complete and quenched with 5 mL of aquous KHSO$_4$. The compound was extracted with diethyl ether and used without any further purification.

For introduction of the reduced bond in the peptide sequence, the peptide was synthesized, as in Example 2, on an automated peptide synthesizer CEM Liberty up to the arginine involved in the reduced bond. After deprotection of the Fmoc group with 20% piperidine/DMF, a solution of 3 eq of Fmoc-phenylalaninal in 5 mL 1% AcOH in DMF was added to the peptide supported on the resin in a syringe. Then 3 eq of NaBH$_3$CN were added portionwise over 1 hour. The reaction was stirred overnight then the resin was washed with DMF and put back on CEM Liberty Synthesizer to complete the sequence.

Cleavage of side-chain protecting groups and from the support was effected using 94:2.5:2.5:1 v/v/v/v TFA/EDT/H$_2$O/iPr$_3$SiH for 2 hours. The peptide/TFA mixture was filtered to remove the support and the peptide/TFA mixture was diluted with water and washed with Et$_2$O (5-times) and the aqueous layer lyophilized.

After purification the peptides were conjugated to TBMB and assayed for inhibition of kallikrein activity, as follows:

Enzymes were purchased from Sigma Aldrich and substrates from Bachem AG. The assay buffer is composed of 10 mM Tris pH 7.4, 150 mM NaCl, 10 mM MgCl$_2$, 1 mM CaCl$_2$, 0.1% BSA, 0.01% Triton X100 and 5% DMSO. Enzymes are incubated with inhibitors for 30 minutes at RT prior to addition of substrate. All experiments were recorded at 30° C. for 90 minutes.

Assays were performed on a BMG Pherastar plate reader at wavelengths of exc/em 350/450 nm. Kallikrein was bought as a solution of 1080 μg/mL and diluted to a working concentration of 0.3 nM in assay buffer. Substrate Z-Phe-Arg-amc was solubilised at the stock concentration of 10 mM in DMSO and diluted to a working concentration of 300 μM with assay buffer. Inhibitors were solubilised in assay buffer to a stock concentration of 60 μM. 50 μL of each reagent is introduced in wells for a final volume of 150 μL per well. Final concentration of kallikrein in assay is 0.1 nM and substrate is 100 μM.

Final concentrations of inhibitors were: 0.5 nM, 1 nM, 2 nM, 5 nM, 8 nM, 10 nM, 20 nM, 50 nM, 80 nM, 100 nM, 200 nM, 500 nM, 800 nM, 1 μM, 2 μM, 5 μM, 8 μM, 10 μM and 20 μM. The initial rate of the reaction is obtained by plotting fluorescence=f (time) data and by fitting a linear trendline for each concentration of inhibitor. The inhibition curves are obtained by plotting initial rate=f ([I]) and $IC_{50}$ values can be evaluated.

This revealed that all of the peptides inhibited the activity of kallikrein; the values for H-ACSDRfRNCPADEALCG-OH (SEQ ID No. 15), H-ACSDRF-(NMeArg)-NC-PADEALCG-OH (SEQ ID No. 16) and H-ACSDRFY[CH$_2$NH]RNCPADEALCG-OH (SEQ ID No. 17) peptides were respectively 4 μM, 3.1 μM, 16.6 μM.

However the backbone alteration also led, as expected, to an increased resistance to proteolysis (for methods see Example 2). Using the highest trypsin concentrations (0.1 μg) described in Example 2, where the PK 15 TBMB conjugate is completely cleaved within 5 min at R7, all three (back-bone modified) peptide TBMB conjugates were uncleaved. Indeed with 1 μg trypsin, and after 1 hour, there was little or no cleavage of any of the backbone-modified TBMB conjugates. Using the highest chymotrypsin concentrations (0.1 μg) described in Example 2, where the PK15 TBMB conjugate is about 50% cleaved after 1 hr, all three back-bone modified peptide TBMB conjugates were uncleaved. With 1 μg chymotrypsin, where the PK 15 TBMB conjugate is completely cleaved after 1 hour, the backbone-modified conjugates were largely (75-85%) intact.

Thus the back-bone modified conjugates have improved stability to proteases, albeit with some loss of binding affinity to the target.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for preparing one or more peptide ligands, comprising polypeptides covalently linked to tris-(bromomethyl) benzene (TBMB) at two or more amino acid residues, comprising the steps of:
   (a) displaying one or more peptide ligand in a phage display system, wherein the displayed polypeptide comprises two or more reactive groups, wherein the two or more reactive groups are conjugated to TBMB to form a covalent linkage to TBMB, and at least one loop which comprises a sequence of two or more amino acids subtended between two of said reactive groups;
   wherein the TBMB is present at less than 100 μM during conjugating to the phage displayed polypeptide;
   (b) exposing the phage displayed peptide ligands covalently linked to TBMB to one or more proteases; and
   (c) screening the phage displayed peptide ligands covalently linked to TBMB for binding against a target, and selecting the phage displayed peptide ligands covalently linked to TBMB which bind to the target.

2. The method of claim 1, wherein the phage displayed peptide ligands covalently linked to TBMB selected for binding to the target are resistant to protease cleavage.

3. The method of claim 1, wherein exposure to the one or more proteases is carried out in the presence of a reducing agent.

4. The method of claim 1, wherein the one or more peptide ligand is a repertoire of peptide ligands.

5. The method of claim 1, wherein the phage displayed peptide ligands covalently linked to TBMB selected for binding to the target are susceptible to protease cleavage.

6. The method of claim 5, wherein exposure to the one or more proteases is carried out in the presence of a reducing agent.

7. The method of claim 5, wherein the one or more peptide ligands is a repertoire of peptide ligands.

8. The method of claim 1, wherein the binding specificity of the phage displayed peptide ligands covalently linked to TBMB for the target is altered though protease cleavage of one or more peptide loops.

9. The method of claim 1, wherein the phage displayed peptide ligands covalently linked to TBMB which bind to the target are further modified by (a) amino acid side chain modification or substitution; or (b) polypeptide backbone modification.

10. The method of claim 9, wherein the backbone modification is selected from the group consisting of introducing, near the site of protease cleavage, a D-amino acid, a reduced peptide bond, and N-methylation.

* * * * *

SEQUENCE LISTING

```
<160> NUMBER OF SEQ ID NOS: 17

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Cys Phe Asn Ser Glu Trp Ser Cys Leu Gln Ser Cys Ser Asn Cys
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Ile Gln Gly Arg
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Ile Asn Gly Arg
1

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Gln Thr Ser Lys Leu Thr Arg Ala Glu Ala Val Phe
```

```
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

```
Ser Phe Asn Asp Phe Thr Arg Val Val Gly Gly Glu
1               5                   10
```

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

```
Leu Phe Ser Ser Met Thr Arg Val Val Gly Phe Leu Val
1               5                   10
```

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

```
Lys Ile Pro Pro Arg Ile Val Gly Gly Thr
1               5                   10
```

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

```
Leu Glu Val Leu Phe Gln Gly Pro
1               5
```

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

```
Ile Glu Gly Arg Gly Ile
1               5
```

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

```
Leu Val Pro Arg Gly Ser
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Leu Val Pro Lys Gly Ser
1               5

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Ser Cys Glu Leu Trp Asn Pro Lys Cys Arg Leu Ser Pro Phe Glu Cys
1               5                   10                  15

Lys Gly

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Ser Cys Val Arg Phe Gly Trp Thr Cys Asp Asn Ser Trp His Gly Cys
1               5                   10                  15

Lys Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide

<400> SEQUENCE: 14

Ala Cys Ser Asp Arg Phe Arg Asn Cys Pro Ala Asp Glu Ala Leu Cys
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa= D-Phenylalanine

<400> SEQUENCE: 15

Ala Cys Ser Asp Arg Xaa Arg Asn Cys Pro Ala Asp Glu Ala Leu Cys
1               5                   10                  15

Gly
```

```
<210> SEQ ID NO 16
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa= N-Methyl-Argenine

<400> SEQUENCE: 16

Ala Cys Ser Asp Arg Phe Xaa Asn Cys Pro Ala Asp Glu Ala Leu Cys
1               5                  10                 15

Gly

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(7)
<223> OTHER INFORMATION: There is a reduced peptide between amino acid
      Phe (position 6) and Arg (position 7)

<400> SEQUENCE: 17

Ala Cys Ser Asp Arg Phe Arg Asn Cys Pro Ala Asp Glu Ala Leu Cys
1               5                  10                 15

Gly
```